US005525305A

United States Patent [19]

Minekus et al.

[11] Patent Number: 5,525,305

[45] Date of Patent: Jun. 11, 1996

[54] IN VITRO MODEL OF AN IN VIVO DIGESTIVE TRACT

[75] Inventors: Mannes Minekus, Zeist; Robert Havenaar, Ijsselstein, both of Netherlands

[73] Assignee: Nederlandse Organisatie voor Toegepast-Natuurwetenschappelijk Onderzoek TNO, Delft, Netherlands

[21] Appl. No.: 256,246

[22] PCT Filed: Nov. 1, 1993

[86] PCT No.: PCT/NL93/00225

§ 371 Date: Jul. 5, 1994

§ 102(e) Date: Jul. 5, 1994

[87] PCT Pub. No.: WO94/09895

PCT Pub. Date: May 11, 1994

[30] Foreign Application Priority Data

Nov. 2, 1992 [NL] Netherlands .......................... 9201907

[51] Int. Cl.[6] .......................... G05D 21/02; B01F 13/00; C12M 1/36; C12M 1/02

[52] U.S. Cl. .......................... 422/111; 366/149; 366/219; 422/129; 422/224; 435/286.1; 435/286.5; 435/286.6; 435/287.1; 435/297.4

[58] Field of Search .................................. 422/129, 189, 422/224, 240, 111; 435/289, 316, 819; 366/150, 69, 151

[56] References Cited

U.S. PATENT DOCUMENTS

| | | | |
|---|---|---|---|
| 3,656,716 | 4/1972 | Ljungerg et al. | 366/75 |
| 4,537,860 | 8/1985 | Tolbert et al. | 435/240 |

FOREIGN PATENT DOCUMENTS

| | | |
|---|---|---|
| 2152452 | 4/1973 | France . |
| 2158118 | 6/1973 | France . |
| 4042298 | 7/1992 | Germany . |
| 55-92130 | 7/1980 | Japan . |
| 62-117621 | 5/1987 | Japan . |
| 62-198433 | 9/1987 | Japan . |
| 597214 | 1/1948 | United Kingdom . |

*Primary Examiner*—Robert J. Warden
*Assistant Examiner*—Robert Carpenter
*Attorney, Agent, or Firm*—Young & Thompson

[57] ABSTRACT

A reactor system suitable in particular for a model of a gastrointestinal tract comprises one or more units (1), each having two or more pressure chambers (2, 3) and in each of the pressure chambers a hose (5) made of flexible material and open at both ends, which hoses are fixed with their ends sealed in such a way that the spaces (6) between the wall of the pressure chambers and the hoses are closed. Connectors (8, 9) are also present for supplying a gas or liquid to and discharging it from the spaces (6) between the wall of the pressure chambers and the hoses, and couplers are present for coupling the pressure chambers to each other and/or to end pieces or intermediate pieces (4). Finally, connectors (10, 11) are present in the end pieces or intermediate pieces for supplying constituents to and discharging them from the hoses.

3 Claims, 3 Drawing Sheets

IN VITRO MODEL OF AN IN VIVO DIGESTIVE TRACT

The invention relates to a reactor system comprising an in vitro model of an in vivo digestive tract.

Reactor systems often consist of a pot or tank in which a stirring element is disposed. The digestion process in the gastrointestinal tract, for example, can be simulated only very imperfectly with such a system. In particular, the peristaltic movements which contribute to the homogenization and transfer of substances are absent.

The object of the invention is to provide a peristaltically mixing reactor system in which in particular highly viscous liquids can be mixed and homogenized, and which system is suitable in particular for assembling a model for a gastrointestinal tract.

According to the invention, the reactor system comprises for this purpose:

- at least one unit consisting of two or more pressure chambers; in each of the pressure chambers a hose made of flexible material and open at both ends, which hoses are fixed with their ends sealed in such a way that the spaces between the wall of the pressure chambers and the hoses are closed;
- connection means for supplying a gas or liquid to and discharging it from the spaces between the wall of the pressure chambers and the hoses; coupling means for coupling the pressure chambers to each other and/or to end pieces or intermediate pieces;
- connection means in the end pieces or intermediate pieces for supplying constituents to and discharging them from the hoses.

The medium in the spaces between the wall of a pressure chamber and a hose can also be used for heating of the constituents taking part in the reaction.

In order to be able to control both the frequency and the force of the peristaltic movements accurately, control means can be used to raise and lower the pressure in the closed spaces between a pressure chamber wall and a hose. These control means will usually consist of computer-controlled pumps.

The volume of the reactor system can be adapted to requirements, through the fact that the number of pressure chambers per unit and the number of units can be varied. The system is preferably modular, i.e. the supply of constituents to and discharge thereof from the system can be handled by means of standardized end pieces and intermediate pieces and the system can be expanded in a simple way, inter alia by means of a peristaltic flap valve pump based on the principle of the invention.

It is pointed out that Abstract 5592130 from Japanese Patent Application 55-2924 discloses a mixer consisting of two bags connected to each other by means of an intermediate piece with channels recessed therein. This intermediate piece also comprises supply and discharge pipes. The mixing is effected by reducing and increasing the volume of the bags alternately, in the course of which the contents are constantly moved from one bag to the other and back. There is no question in this case of pressure chambers in which hoses made of flexible material and open at both ends are fitted, so that any desired number of pressure chambers cannot be connected to each other or to intermediate or end pieces either. This known mixer is therefore not suitable for forming a reactor system which through its modular construction can be extended as desired.

In the case of several reactor units, in successive units the discharge pipe for mixed constituents of the first unit can be connected to the supply pipe for constituents for mixing in a second unit, and computer-controlled valves can be fitted in the combined discharge and supply pipes.

With such a reactor system, an in vitro model of the gastrointestinal tract with a high degree of correspondence to the in vivo situation can be constructed. Particles can be pulverized through powerful contractions. The mechanical cleansing effect in the small intestine, which is essential for preventing excessive microbiological growth, can be simulated extremely well with the reactor. It is possible to work with highly viscous liquids such as culture media, the gastrointestinal contents from a regular meal, or the contents of the large intestine. The absence of projecting parts such as stirrers and the presence of a flexible wall greatly reduce the growth of organisms. Friction-sensitive cells can be grown by selecting gentle contractions.

The flexible hoses are preferably made of silicone rubber.

The exchange of nutrients, production and waste products, liquids and gases can be achieved through the use of semi-permeable hoses. This also applies if at least one unit is connected to a device for the exchange of low-molecular weight components, which device is in particular provided with hollow membrane fibres.

A flexible inner tube can also be fitted in the hose of at least one pressure chamber. Liquid supplied to said flexible tube can exchange substances with dialysis liquid in a space between the hose and the flexible tube.

The contents of the mixing reactor can be brought to any desired temperature (for example to 37° C.) if the reactor is provided with means for heating the liquid or gaseous medium which can be conveyed to the spaces between the wall of the pressure chambers and the hoses.

Moreover, the reactor system according to the invention is suitable not only for an in vitro model of the gastrointestinal tract, but the reactor according to the invention can also be used for the production of polymers, high-density cultures, slurry fermentations and mould fermentations. In general, the reactor system will be of interest for the food industry, the pharmaceutical and biotechnology industry, and in laboratories and education.

One or more pH electrodes will often be placed in the reactor, thus permitting a computer-controlled physiological pH development of the reactor contents. The gradual emptying of the stomach can also be simulated.

The reactor system according to the invention is extremely well suited for complete computer control.

The principle of the invention can also advantageously be used on a peristaltic flap valve pump which is characterized by three or more pressure chambers, each with a flexible hose fixed therein in such a way that the space between the pressure chamber wall and the hose is closed and the hoses are connected to each other, inlet and outlet means for a gas or liquid opening out into each of the closed spaces between a pressure chamber wall and a hose, and control means for controlling the supply of a gas or liquid to and the discharge thereof from the closed spaces between a pressure chamber wall and a hose.

The invention will now be explained in greater detail with reference to the figures.

Figure 1:
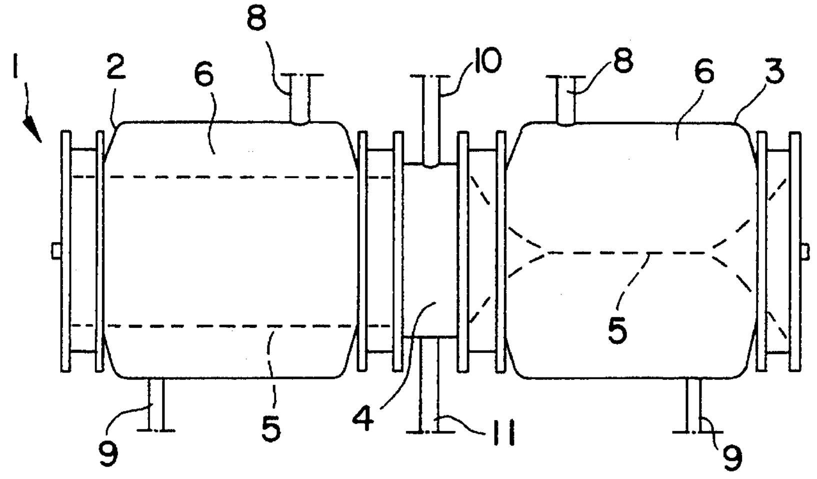
FIG. 1 shows diagrammatically a reactor system according to the invention.

The reactor system shown diagrammatically in FIG. 1 contains a unit 1 consisting of two cylindrical pressure chambers 2 and 3 which are interconnected by means of a cylindrical intermediate piece 4. A hose 5, consisting of, for example, silicone rubber, is fixed in each of the pressure chambers. Situated between the hoses 5 and the walls of the pressure chambers 2 and 3 are closed spaces 6, into each of which an inlet 9 and an outlet 8 opens. The inlet 9 and the outlet 8 can be the same channel.

The fastening of the end edges of the hoses 5 is gastight and liquid-tight.

It can be seen in FIG. 1 that the space 6 of the pressure chamber 3 has been filled by way of the inlet 9 with a gas or liquid under pressure, and that as a result of this the hose 5 is pinched in the chamber 3. A mixture of substances which was present in the hose of the pressure chamber 3 will be driven out of said hose and forced through the intermediate piece 4 into the unpinched hose 5 of the pressure chamber 2. If the gas or liquid filling of the space 6 of the pressure chamber 3 is then discharged through the outlet 8 and the space 6 of the pressure chamber 2 is filled with gas or liquid through the inlet, the contents of the hose 5 of the chamber 2 will flow back again to the hose 5 of the chamber 3. In this way the peristaltic movements of the stomach and the intestinal tract are simulated and good mixing and homogenization of the reactor contents can be produced. For purposes of filling the reactor, a supply pipe 10 opens out into the intermediate piece 4, while for the discharge of materials mixed in the reactor use is made of the discharge pipe 11 extending from the intermediate piece 4. Alternatively, no intermediate piece is placed between the pressure chambers 2 and 3, and an end piece with supply means for the components to be mixed is fitted on the left end face of pressure chamber 2, while an end piece with discharge means for mixed components is fitted on the right end face of pressure chamber 3.

Figure 2:
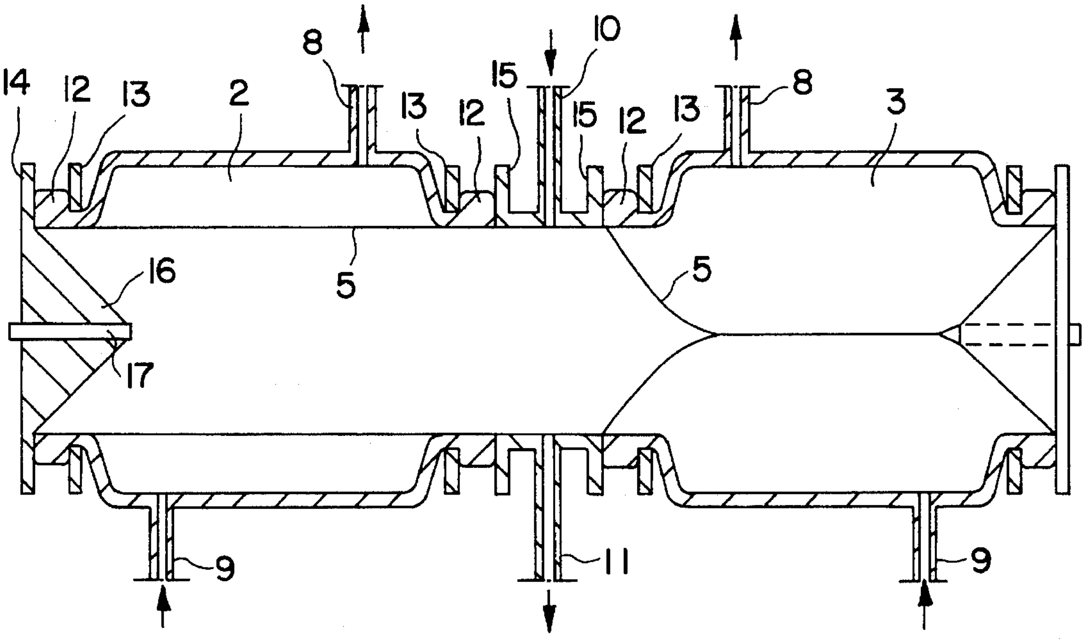
FIG. 2 shows a longitudinal section of a possible constructional embodiment.

A possible constructional embodiment of the reactor according to FIG. 1 can be seen in FIG. 2. Corresponding parts are provided with the same reference numbers.

The end edges of the hoses 5 are passed around flanged edge parts 12 of the casing of the chambers 2 and 3. For fixing of the two pressure chambers 2 and 3 to the intermediate piece 4, a ring 13 is placed in the annular gap next to each of the flanged edge parts 12, and fixing bolts 14 run through openings in said rings 13 and openings in flanges 15 of the intermediate piece 4.

Closing pieces 16 with a pH electrode 17 extending through them are placed at the end faces of the chambers 2 and 3 facing away from each other. The closing pieces 16 are fixed to a ring 13 by means of bolts 14. An intermediate piece 4 with pipes 10 and/or 11 can also be used as the end piece, in which case it is fitted instead of the closing pieces 16.

Figure 3:
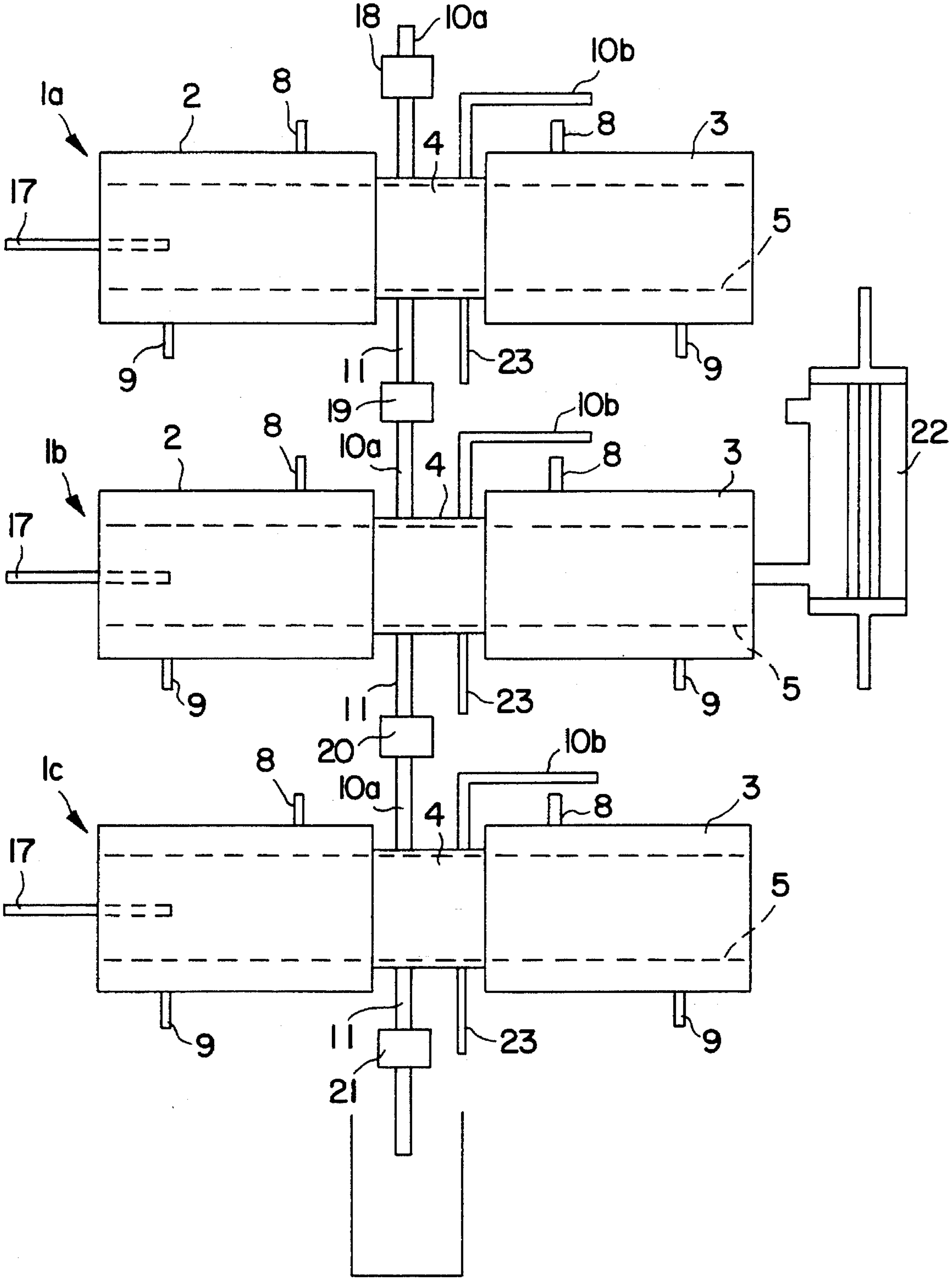
FIG. 3 shows diagrammatically a more extended version of a reactor system according to the invention.

FIG. 3 shows very diagrammatically three successive units 1*a*, 1*b* and 1*c*, forming an in vitro model for the stomach, the duodenum and the jejunum.

The discharge pipe 11 of the first unit 1*a* is integral with the supply pipe 10*a* of the second unit 1*b*, while the discharge pipe 11 of the second unit 1*b* is integral with the supply pipe 10*a* of the third unit 1*c*. Four valves 18, 19, 20 and 21 are shown, by means of which valves the supply and discharge of the substances can be accurately controlled. Each of the units has one or more additional supply pipes 10*b*.

An exchange device 22, consisting of hollow membrane fibres, connects to the second unit 1*b*. Low-molecular weight gases and components can be exchanged by means thereof. Each of the units 1*a*, 1*b*, 1*c* is provided with a port 23 for taking samples. There is a possibility of placing the membrane fibres on the centre of a pressure chamber.

Figure 4:
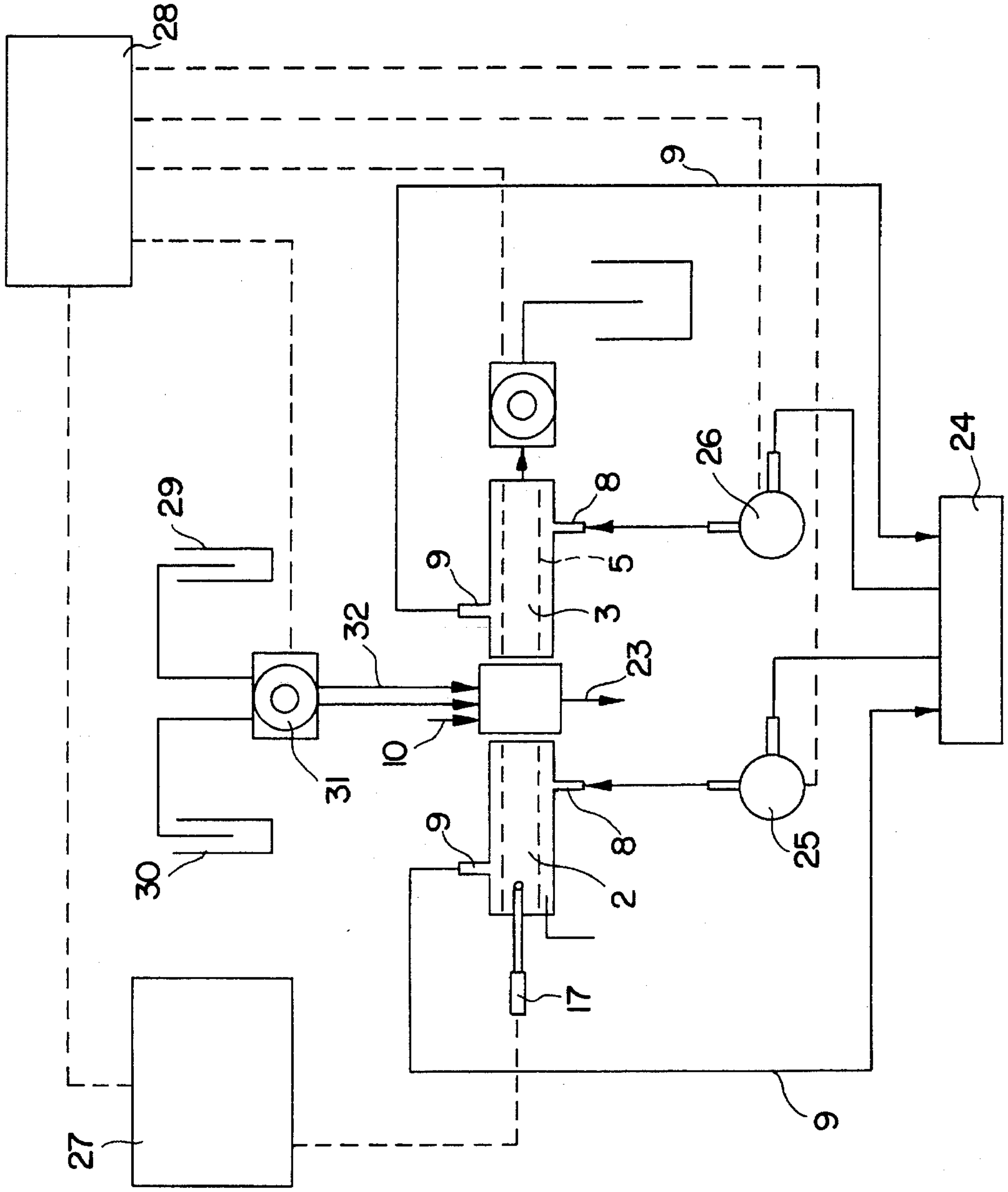
FIG. 4 shows a computer-controlled in vitro stomach model using the reactor system according to the invention.

FIG. 4 is a diagram of an in vitro model of a peristaltic mixing reactor according to the invention.

The water bath to be heated electrically (for example, to 37° C.) is indicated by 24. Warm water can be pumped by pumps 25 and 26 to the inlet of the pressure chambers 2 and 3, and can be fed back to the water bath 24 through the pipes 9. The pH control unit has the reference number 27, and the computer for controlling the whole system is indicated by 28. The computer control lines are indicated by dashed lines. Reference number 29 is a tank for hydrochloric acid (HCl), and 30 is a tank for enzymes. Hydrochloric acid and enzymes can be pumped by means of the pump unit 31 through the pipes 32 and 33 to the intermediate piece 4. Food constituents are introduced through the normal supply inlet 10.

The reactor described can lead to excellent mixing and homogenization of the components with or without damage thereto.

The principle of the invention based on peristalsis can be applied in a peristaltic flap valve pump consisting of three or more chambers 2, 3. The supply of gas or liquid to and the discharge thereof from the closed spaces between a chamber wall and a hose are regulated by, for example, computer-controlled control means. Where three chambers are coupled, in a first phase only the hose of the third chamber can be pinched, in a second phase the hoses of the first and third chamber can be pinched, in a third phase only the hose of the first chamber can be pinched, in a fourth phase the hoses of the first and second chamber can be pinched, and in a fifth phase the hoses of the three chambers can be pinched. In order to make it easy to control the liquid or gas pressure to the space between the chamber wall and the flexible hose in the case of a unit with various chambers placed after one another, and thus to control the peristaltic thrusting movements, use can be made of computer-controlled magnetic valves. It is possible to control not only the times of increasing and reducing the liquid or gas pressure, but also the volumes to be supplied, for example by metering the quantity with the aid of a piston which can be moved in a cylinder between adjustable stops. In FIG. 3 the combination of a discharge pipe 11 and supply pipe 10 and a valve 19 could be replaced by a peristaltic flap valve pump according to the invention which is produced by coupling three chambers 2, 3.

What is essential for the invention of the reactor system according to the invention is that the open hoses are fitted in pressure chambers in which the space between the wall of a pressure chamber and the hose in question can be used not only for pinching said hose, but also for heating the constituents in the hose by means of a liquid or gas in the space. It is also important that coupling means should be present to permit coupling of the pressure chambers to each other and/or to end pieces or intermediate pieces, connection means being present in said end pieces or intermediate pieces, for the purpose of supplying constituents to the hoses and discharging constituents from them.

We claim:

1. An in vitro model of an in vivo digestive tract, comprising:

at least one unit including at least two pressure chambers;

each of the pressure chambers having a hose made of flexible material having two ends and open at both ends, which hoses are fixed with their ends sealed in such a way that spaces between walls of the pressure chambers and the hoses are closed, means for supplying a fluid to and discharging it from the spaces between the wall of the pressure chambers and the hoses and for controlling the raising and lowering of the pressure in said closed spaces, at least one intermediate piece coupled between two pressure chambers, end pieces for closing the ends of each unit, at least one supply line for gastrointestinal contents into a pressure chamber, at least one supply line a source of enzymes, fluidly connected to said source of enzymes for introduction of said enzymes into a pressure chamber, at least one pH-electrode for determining the pH inside a unit and controlling means for controlling the physiological pH-development of the reactor contents, and at least one discharge line for discharging the contents of the in vitro model.

2. An in vitro model according to claim 1, wherein at least one said unit is connected to a device for the exchange of low-molecular weight components, which device is provided with hollow membrane fibers.

3. An in vitro model according to claim 1, further comprising means for heating the fluid medium which can be conveyed to the spaces between the walls of the pressure chambers and the hoses.

* * * * *